United States Patent [19]
Karger et al.

[11] Patent Number: 6,068,749
[45] Date of Patent: May 30, 2000

[54] SUBATMOSPHERIC, VARIABLE PRESSURE SAMPLE DELIVERY CHAMBER FOR ELECTROSPRAY IONIZATION/MASS SPECTROMETRY AND OTHER APPLICATIONS

[75] Inventors: Barry L. Karger, Newton; Frantisek Foret, Malden; Daniel P. Kirby, Milton, all of Mass.

[73] Assignee: Northeastern University, Boston, Mass.

[21] Appl. No.: 08/784,400

[22] Filed: Jan. 17, 1997

Related U.S. Application Data
[60] Provisional application No. 60/010,242, Jan. 19, 1996.

[51] Int. Cl.[7] .................. G01N 27/26; G01N 27/447
[52] U.S. Cl. .................. 204/452; 204/451; 204/601; 204/603; 250/282; 250/288; 250/289
[58] Field of Search .................. 250/288, 281, 250/282, 289; 204/452, 601, 603, 451

[56] References Cited

U.S. PATENT DOCUMENTS

| | | | |
|---|---|---|---|
| Re. 34,757 | 10/1994 | Smith et al. | 204/299 R |
| 4,209,696 | 6/1980 | Fite | 250/281 |
| 4,531,056 | 7/1985 | Labowsky et al. | 250/288 |
| 4,542,293 | 9/1985 | Fenn et al. | 250/288 |
| 4,647,772 | 3/1987 | Lewis et al. | 250/288 |
| 4,842,701 | 6/1989 | Smith et al. | 204/180.1 |
| 4,861,988 | 8/1989 | Henion et al. | 290/288 |
| 4,885,076 | 12/1989 | Smith et al. | 204/299 R |
| 4,935,624 | 6/1990 | Henion et al. | 250/288 |
| 4,977,320 | 12/1990 | Chowdhury et al. | 250/288 |
| 4,994,165 | 2/1991 | Lee et al. | 204/299 R |
| 5,015,845 | 5/1991 | Allen et al. | 250/288 |
| 5,115,131 | 5/1992 | Jorgenson et al. | 250/288 |
| 5,122,670 | 6/1992 | Mylchreest et al. | 250/423 R |
| 5,306,412 | 4/1994 | Whitehouse et al. | 204/299 R |
| 5,358,613 | 10/1994 | Schneider et al. | 204/180.1 |
| 5,423,964 | 6/1995 | Smith et al. | 204/180.1 |
| 5,447,617 | 9/1995 | Shieh | 204/299 R |
| 5,504,327 | 4/1996 | Sproch et al. | 250/288 |
| 5,504,329 | 4/1996 | Mann et al. | 250/288 |
| 5,543,618 | 8/1996 | D'Silva | 250/288 |
| 5,571,398 | 11/1996 | Karger et al. | 204/603 |
| 5,572,023 | 11/1996 | Caprioli | 250/288 |
| 5,580,434 | 12/1996 | Robotti et al. | 204/451 |
| 5,652,427 | 7/1997 | Whitehouse et al. | 250/288 |

OTHER PUBLICATIONS

Richard D. Smith et al., "Improved Electrospray Ionization Interface for Capillary Zone Electrophoresis–Mass Spectrometry," *Anal. Chem.* vol. 60:1948–1952 (1988).

Michael G. Ikonomou et al., "Investigations of the Electrospray Interface for Liquid Chromatography/Mass Spectrometry," *Anal. Chem.* vol. 62:957–967 (1990).

Matthias Mann, "Electrospray: Its potential and Limitations as an Ionization Method for Biomolecules," *Organic Mass Spectrometry* vol. 25:575–587 (1990).

Richard D. Smith et al., "New Developments in Biochemical Mass Spectrometry: Electrospray Ionization", *Analytical Chemistry* vol. 62:No. 9 May 1 (1990).

Primary Examiner—Robert J. Warden, Sr.
Assistant Examiner—Kaj K. Olsen
Attorney, Agent, or Firm—Weingarten, Schurgin, Gagnebin & Hayes LLP

[57] ABSTRACT

A subatmospheric, variable pressure sample delivery chamber, useful as an electrospray ionization device for introducing a sample into a mass spectrometer or as a sample delivery device for delivery of a sample to a collection device at subatmospheric pressures, is disclosed. The sample delivery chamber is configured to maintain an operating pressure between 1 and 750 Torr, preferably between 50 and 700 Torr. The chamber has an inlet port for introduction of a gas and an exit port capable of being coupled either to a sampling orifice for an analytical device, usually a mass spectrometer, or directly to a pump for removal of gas. A sample delivery device extends from outside the chamber into the interior of the chamber. The inlet end of the sample delivery device is capable of receiving a sample and the exit end of the sample delivery device is aligned with the exit port of the chamber, if the sample is to be delivered to an external analytical device, or aligned with the collection device, for direct collection of the sample.

34 Claims, 7 Drawing Sheets

SUBATMOSPHERIC, VARIABLE PRESSURE SAMPLE DELIVERY CHAMBER FOR ELECTROSPRAY IONIZATION/MASS SPECTROMETRY AND OTHER APPLICATIONS

RELATED APPLICATIONS

This application claims priority from U.S. Provisional Application Ser. No. 60/010,242, filed Jan. 19, 1996, the whole of which are hereby incorporated by reference herein.

GOVERNMENT RIGHTS

Part of the work leading to this invention was carried out with United States Government support provided under a grant from the National Institutes of Health, Grant No. GM 15847. Therefore, the U.S. Government has certain rights in this invention.

FIELD OF THE INVENTION

This invention relates to the introduction of a sample into an analytical device and particularly to the use of an electrospray process to introduce a sample into a mass spectrometer.

BACKGROUND OF THE INVENTION

Electrospray ionization, a process in which a liquid is subjected to a strong electric field and is formed into a stream of small, charged droplets leading to sample ionization in the gas phase, is one of the most versatile ionization techniques for the investigation of macromolecules. The electrospray ionization process has recently found application as a means of producing ions for mass spectrometric analysis. (See, e.g., Smith et al., *Anal. Chem.* 62:885, 1990; Mann, Organ. Mass Spec. 25:575, 1990; Henion et al., U.S. Pat. No. 4,861,988; Allen et al., U.S. Pat. No. 5,015,845.) Today, electrospray ionization mass spectrometry (ESI-MS) is a widely used technique in biological, biochemical, pharmaceutical and medical research for studying complex biological samples containing species such as peptides, protein, carbohydrates or nucleic acids. The information on a sample that such an ESI-MS system can provide can be further enhanced by on-line combination with a microseparation technique, such as capillary electrophoresis, capillary electrochromatography or microcolumn liquid chromatography. Unfortunately, however, in many cases, the routine use of ESI-MS is still limited by relatively time consuming optimization of operational conditions and by insufficient sensitivity.

Recent advances in the design of electrospray devices have led to the improvement in efficiency of the electrospray sample ionization process and, at the same time, to a decrease in the total consumed sample amount. In a typical application, a sample in liquid solution and usually, but not always, in ionic form is fed through a metallic needle held at high potential and aimed at an entrance port of a mass spectrometer. Typical needles are 100–300 $\mu$m i.d. at 2–8 kV. The electrospray process causes the sample solution to form small, charged droplets which contain sample ions and solvent. The charged droplets ultimately desolvate leaving sample ions, some of which then enter the mass spectrometer for analysis. The electrospray needle is typically placed 1 to 20 mm in front of the mass spectrometer entrance port or sampling orifice, which often is heated to assist in the desolvation process. The needle is usually at high potential and the mass spectrometer at or near ground, although the polarities can be reversed. Current trends are to use very small needle tips, metal coated drawn glass with internal diameters of 1–10 $\mu$m or even in the submicrometer range. This helps to utilize the sample more effectively by transferring the generated ions more efficiently to the mass spectrometer. Typically, a metalized glass micropipette is used as both the sample reservoir and electrospray needle. Extremely low sample flow rates (low nL/min) are generated by the electrospray action.

While microelectrospray (sometimes also called nanoelectrospray) seems to work very well for infusion studies, its use for coupling of capillary electrophoresis (CE) to mass spectrometry is limited to very narrow separation capillaries with the electrospray interface operating in the sheathless mode. Coupling of a more standard (routinely used) larger bore (50–100 $\mu$m i.d.) CE capillary to a microelectrospray may require the use of a liquid junction type of interface with a flow of a supporting liquid solution, such as 1% acetic acid in 50% methanol. (See, Lee et al., U.S. Pat. No. 4,994,165.) The use of a pump, necessary for pumping of the spray solution through the electrospray needle, generates significant pressure at the junction point and can result in reverse liquid flow in the CE capillary. Although a counterpressure can be applied at the injection end of the CE capillary, this approach is not very practical since significant experimentation must be performed to find the proper counterpressure, and any change in the system settings (e.g., blockage of the electrospray interface capillary, change of its length or change of the buffer viscosity) will require another time consuming optimization process.

SUMMARY OF THE INVENTION

We have now designed and evaluated a subatmospheric, variable pressure sample delivery chamber, which is useful as an electrospray ionization interface for a mass spectrometer. The sample delivery chamber of the invention is also useful without electrospray ionization for subatmospheric delivery of a sample, e.g., directly to a collection device contained within the chamber. Subatmospheric operating pressures of between 1 and 750 Torr are contemplated, with pressures between 50 and 700 Torr preferred.

Thus, the invention generally features a sample delivery chamber that is configured for removal of gas to subatmospheric pressures. The chamber has an inlet port for introducing a gas into the chamber and an exit port for withdrawing gas from the chamber. The chamber also has a sample delivery device extending from outside the chamber into the chamber interior.

Preferably, the sample delivery device is a capillary tube, or a microchip containing a groove or channel through which a sample can be delivered. The exit end of the sample delivery device preferably has an inside diameter that is less than the average inside diameter of the sample passage through the device.

In the electrospray ionization mode, the exit port of the chamber is configured for attachment to a mass spectrometer, or other analytical device, external to the chamber, and the exit end of the sample delivery device is aligned with the chamber exit port. When the sample delivery chamber of the invention is configured for direct sample collection, the exit port of the chamber is coupled to a pump for gas removal, and a collection device, which is most preferably a movable system of collection capillaries but which could be a collection membrane, is positioned within the chamber and adjacent to the exit end of the sample delivery device.

Control of the flow rate through the sample delivery device, e.g., an electrospray needle, by pressure regulation at its exit end, as in the sample delivery chamber of the invention, eliminates the need for time consuming pressure balancing optimization at the sampling end, as required by certain prior art configurations. When used as an electrospray ionization mass spectrometry interface, the sample delivery chamber of the invention also permits more precise directing of the electrospray generated ions into the sampling orifice of the mass spectrometer.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 1b is a perspective view of an alternative configuration for a sample delivery device for the embodiment of the invention shown in FIG. 1a;

FIG. 1c is an end view of the sample delivery device of FIG. 1b;

FIG. 1d shows an air flow pattern formed in the operation of the embodiment of the invention of FIG. 1a;

FIG. 2b is a total ion electropherogram and selected ion monitoring traces of the separated sample described in FIG. 2a;

FIG. 3 is a graph showing a mass spectrometer ion signal plotted versus pressure in the sample delivery chamber of the embodiment of FIG. 1a.

DESCRIPTION OF THE PREFERRED EMBODIMENTS

The subatmospheric, variable pressure sample delivery chamber of the invention is particularly useful when configured as an electrospray ionization mass spectrometer interface and coupled to, e.g., a separation capillary such as in the technique of capillary electrophoresis. In the example shown in FIG. 1a, a subatmospheric electrospray interface device consists of a subatmospheric chamber (2), which has an inlet port (4), for introducing a gas into the chamber, and an exit port (6), coupled to a sampling orifice (8) for a mass spectrometer (9). An electrospray needle (10) extends from outside the chamber into the interior of the chamber through inlet port (4). The inlet end (12) of electrospray needle (10) is capable of receiving a sample to be delivered into a mass spectrometer, and the electrospray tip (14) is aligned with the chamber exit port (6). Electrospray needle (10) is preferably formed from a narrow (1–20 μm i.d.) fused silica capillary, which can be metalized or left non-metalized. When desirable, the electrospray tip (14) can be further shaped by grinding, etching or heat pulling to provide a sharp spray point. In the embodiment depicted, the sampling end (12) of the electrospray needle is aligned with the exit end of an electrophoresis capillary (16) in an electrode buffer reservoir (18).

Figure 1A:
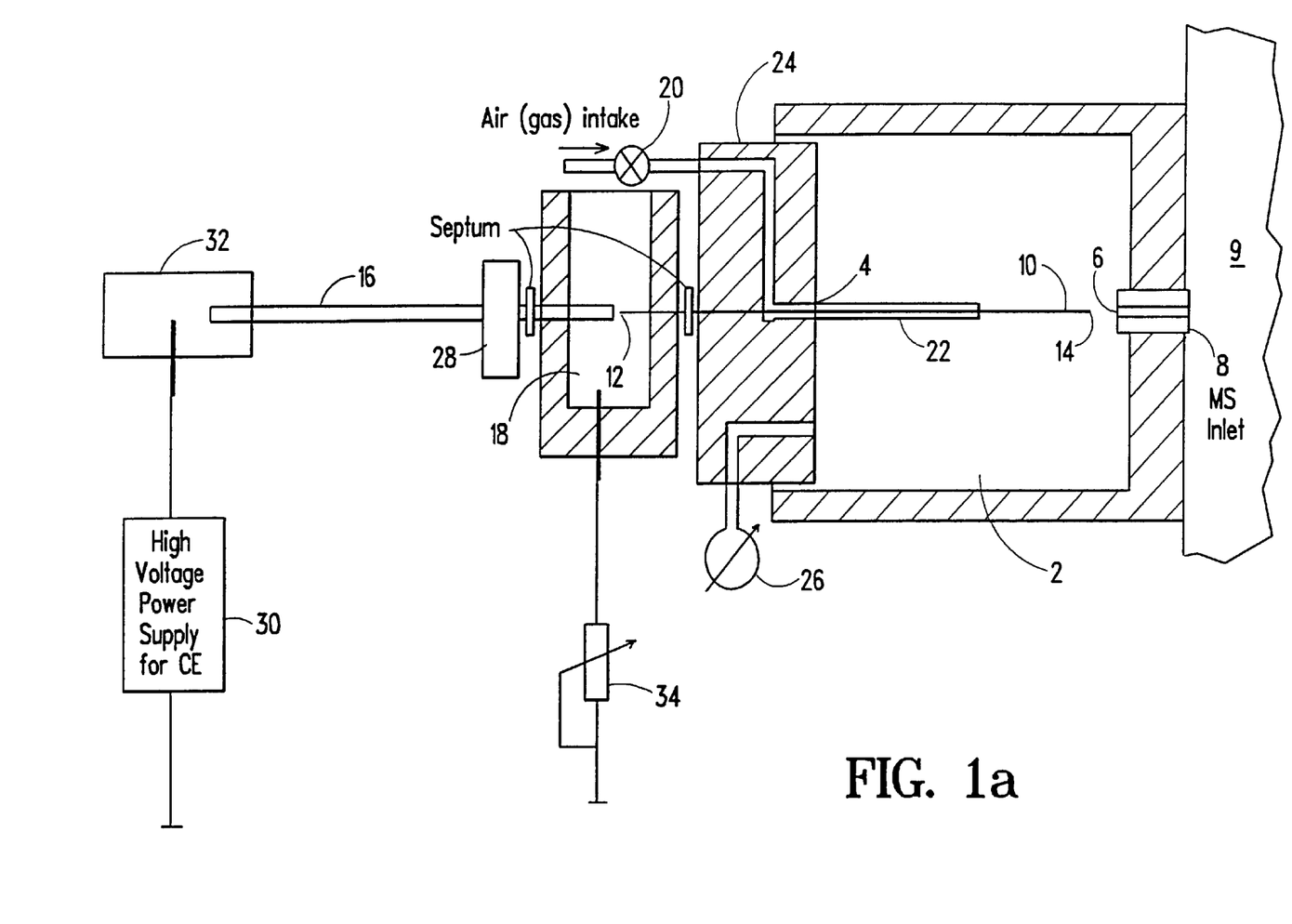
FIG. 1a is a section through a side schematic view of one embodiment of the invention in which a subatmospheric, variable pressure sample delivery chamber, configured as an electrospray ionization mass spectrometer interface, is coupled to an electrophoresis capillary.
Figures 1B, 1C:
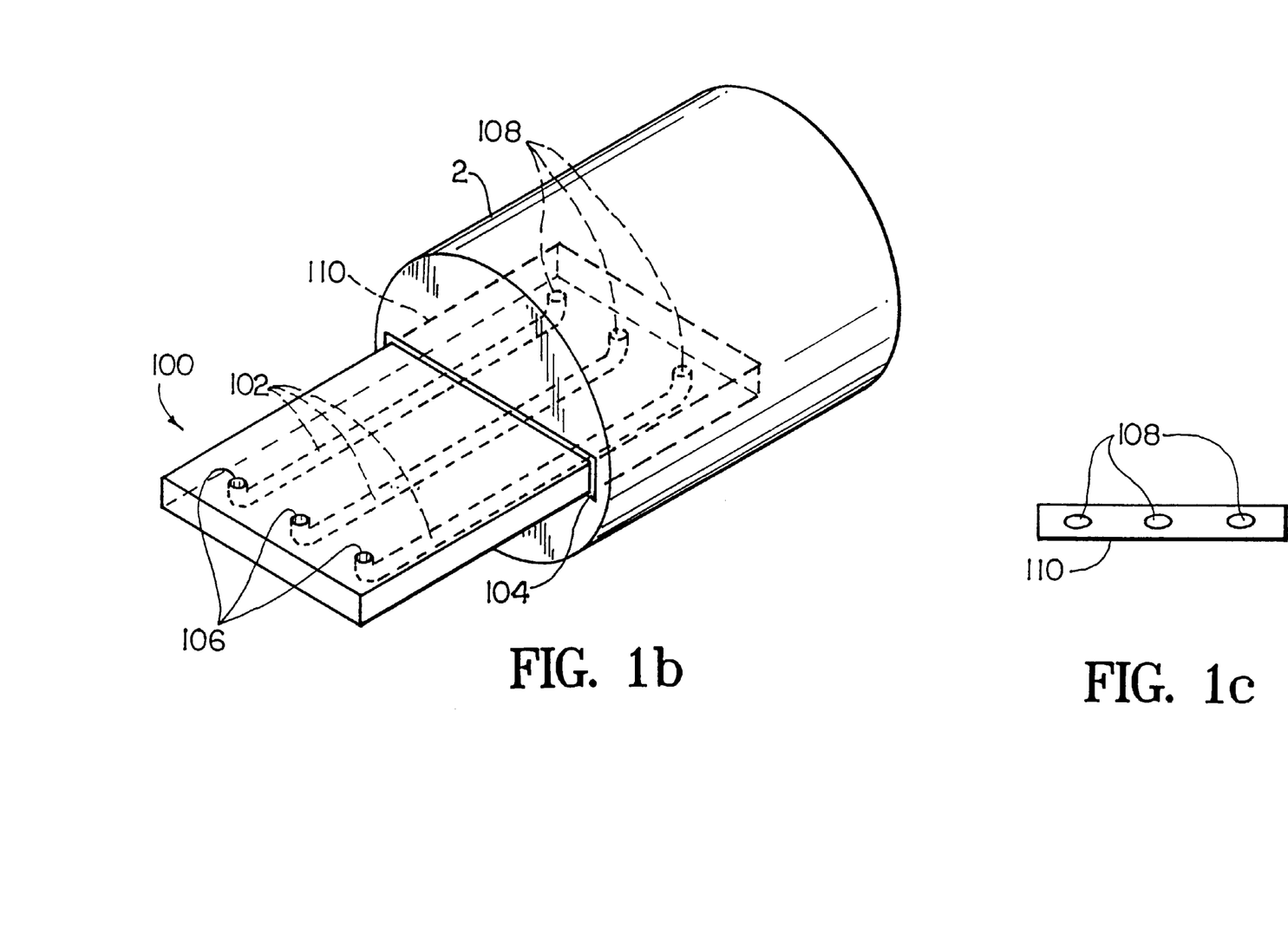

Alternatively, an electrospray needle or sample delivery device could be formed from a fused silica microchip, as shown in FIGS. 1b and 1c. In this example, a fused silica microchip (100), such as disclosed in U.S. patent appl. Ser. No. 08/675,177, now U.S. Pat. No. 5,872,010, hereby incorporated by reference, is attached to subatmospheric chamber (2) via a pressure sealing insert (e.g., silicone rubber) (104). Microchip (100) has one or more parallel sample delivery channels (102), each channel having a sample delivery inlet opening (106) and an electrospray opening (108). The face (110) of microchip (100) surrounding electrospray opening (108) can optionally be coated with a non-wetting, hydrophobic material. Capillary electrophoresis can be carried out in the channels of the chip or the chip can serve solely as a sample delivery device, e.g., for a sample from an attached system.

The flow rate through the electrospray needle is controlled by regulating the pressure in chamber (2) in the following manner. As a vacuum (gas pressure of less than 10 mTorr) is applied to mass spectrometer (9), gas flow is initiated out of chamber (2) into mass spectrometer (9) via coupled chamber exit port (6) and sampling orifice (8). Electrospray needle (10) is positioned in the stream of gas (air or any supporting gas such as nitrogen, $SF_6$, etc.) entering the electrospray chamber through inlet port (4) via gas input tube (22), which passes through a solid stabilization chamber lid (24). Gas flow is regulated at input valve (20), by controlling gas flow into chamber (2) via inlet port (4), to achieve a gas pressure in chamber (2) of between 1–750 torr, the optimum pressure depending on the diameter of sampling orifice (8). The pressure in the chamber is monitored by a pressure monitor (26).

The ability to control the pressure in the electrospray chamber allows for fine control of the sample flow rate without the necessity of providing a pressure driven flow from the sampling end of the needle. Formation of the electrospray droplets at lower (subatmospheric) pressure also facilitates their better desolvation, allowing the use of a wide range of sizes of electrophoretic capillaries with or without electroosmotic flow.

Figure 1D:
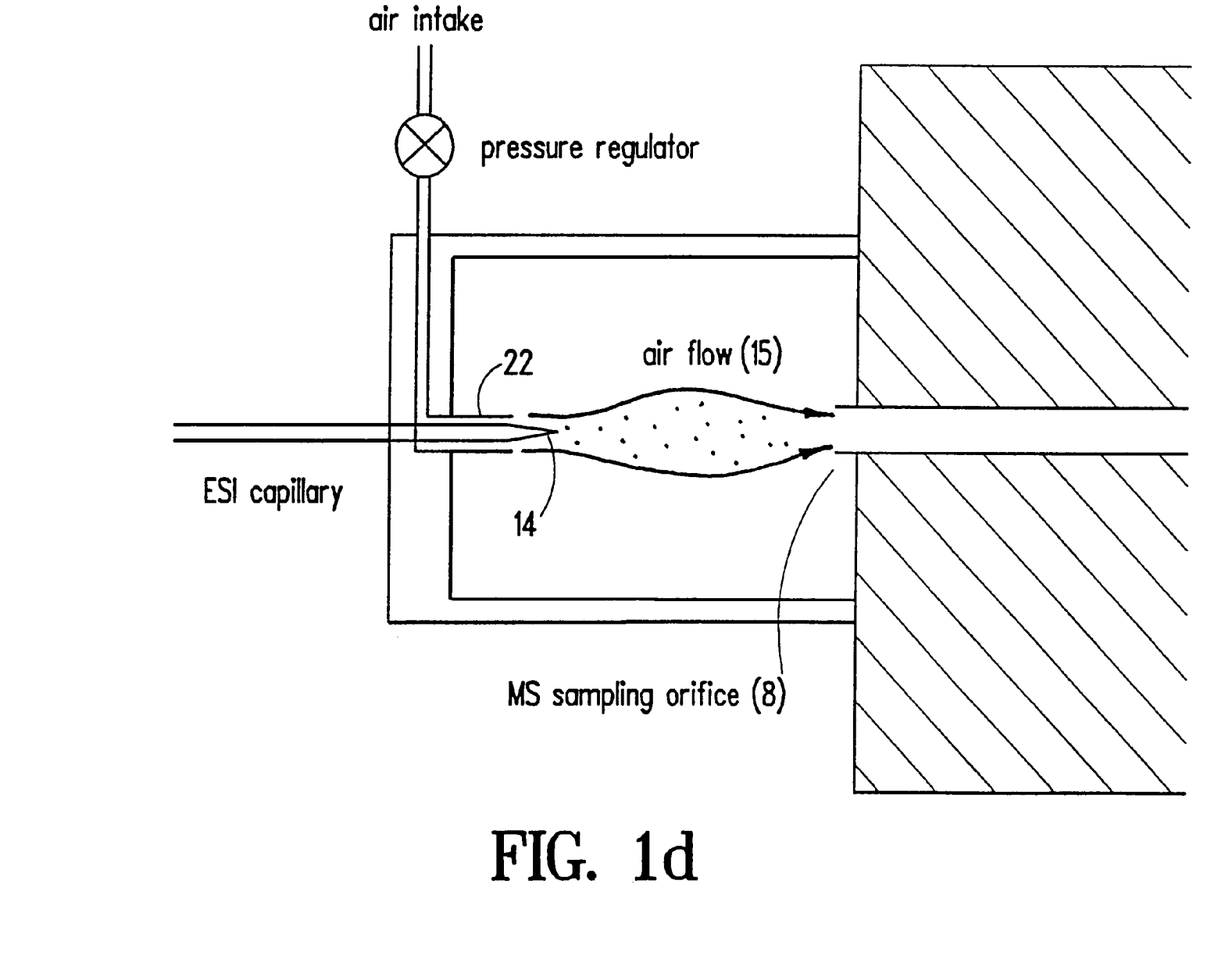

Use of a subatmospheric pressure greater than 10 mTorr, above a true vacuum, in electrospray chamber (2), in conjunction with vacuum pressures (<10 mTorr), and preferably <1mTorr, in mass spectrometer (9), creates a gas flow between the two devices and allows precise directing of the electrospray-generated ions into the entrance port or sampling orifice (8) of the mass spectrometer. As shown in FIG. 1d, the air (gas) streaming through gas input tube (22) flows around electrosprayed droplets emerging from electrospray tip (14), creating air flow pattern (15) and directing the droplets into the mass spectrometer sampling orifice (8). This gas flow helps both in the evaporation of the droplets and in transporting the ions into the mass spectrometer.

To assure minimal efficiency loss of separated bands of the electrophoresis sample, the internal volume of electrospray needle (10) should be comparable to or smaller than the volume of the bands in the separation capillary (16). This small volume can easily be achieved. For example, a 50 mm long, 20 μm i.d. electrospray needle has an internal volume of less than 16 nL while the volume of a typical zone in the 75 μm CE capillary is ~20–50 nL.

From a practical point of view, it is important to keep the pressure in the electrospray chamber above a certain level to avoid freezing of the electrosprayed liquid, as was observed in earlier attempts to electrospray directly into high vacuum (<10 mTorr) inside the mass spectrometer. For the design described herein, the pressure in the electrospray chamber should be in the range of 1–750 Torr. As the total uptake of the supporting gas into the electrospray chamber is regulated in part through gas input valve (20) rather than solely through the sampling orifice (8) of the mass spectrometer, the size of the orifice (8) can be increased to improve sampling efficiency without loss of vacuum efficiency in the mass spectrometer.

The decoupling of electrospray needle (10) and electrophoretic capillary (16) allows use of different compositions of the buffer for separation and electrospray ionization. For easier monitoring of the CE separation and possible programming of mass spectrometric data acquisition, a fiber-optic based detector cell (28) can be attached close to the exit end of the electrophoretic capillary.

We have separately discovered that capillary electrophoresis/electrospray mass spectrometry can be carried out with only one high voltage power supply (30), which is in contact with electrode buffer input reservoir (32), as shown in FIG. 1a. In a conventional configuration, a separate power supply is used for the electrospray interface itself and was believed to be necessary for electrospray ionization. However, we have determined that a separate power supply is not required for the electrospray interface, since the CE high voltage power supply (30) always generates more current than is consumed by the electrospray process. Instead, a variable resistor (34) can be used for control of the electrospray needle potential. In such a case, the CE power supply (30) would preferentially be operated in the constant current mode, assuring the desired electric field strength in the CE separation capillary. Of course, if desired, two power supplies could also be used with the subatmospheric electrospray interface of the invention.

Figure 2A:
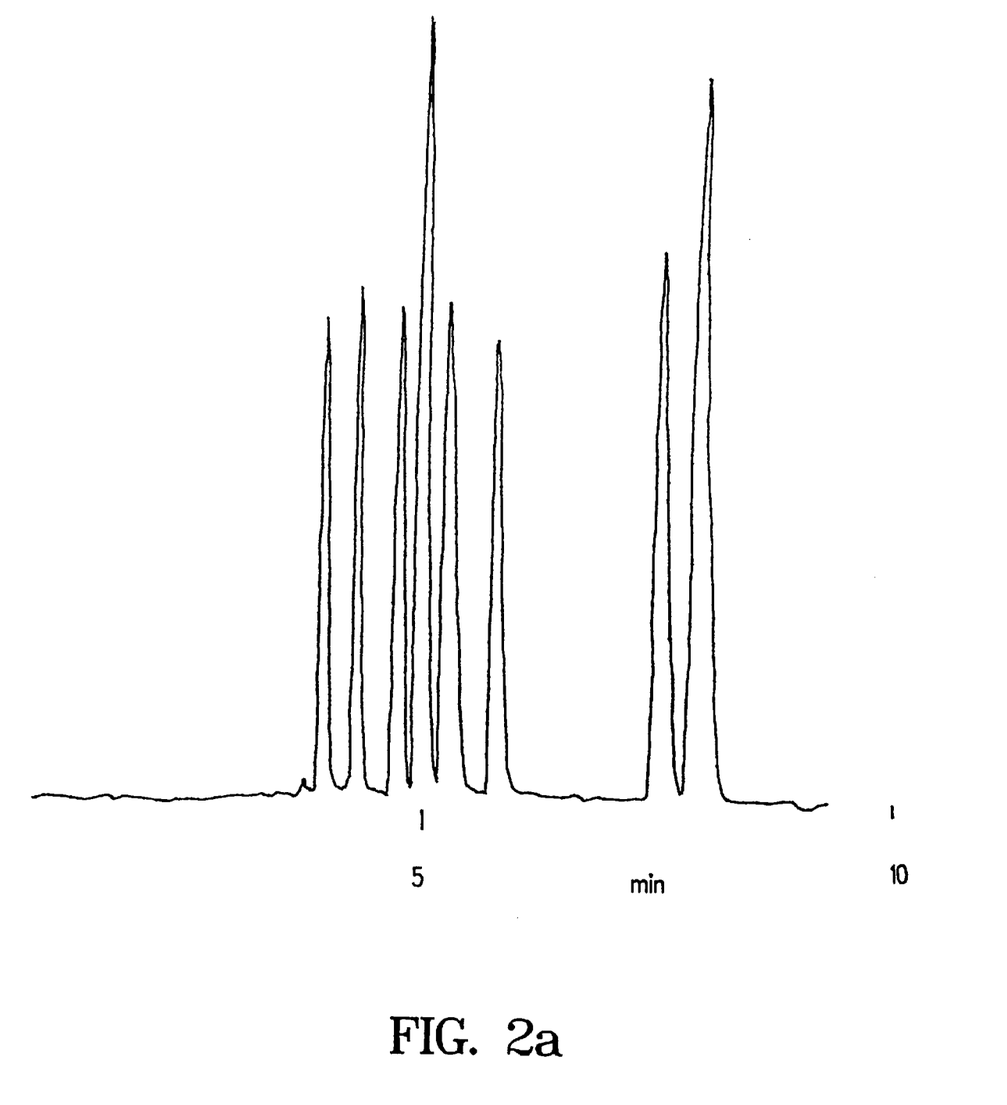
FIG. 2a is a UV trace of a mixture of peptides separated by capillary electrophoresis according to the embodiment of the invention shown in FIG. 1a, as monitored by a fiber optic detector.
Figure 2B:
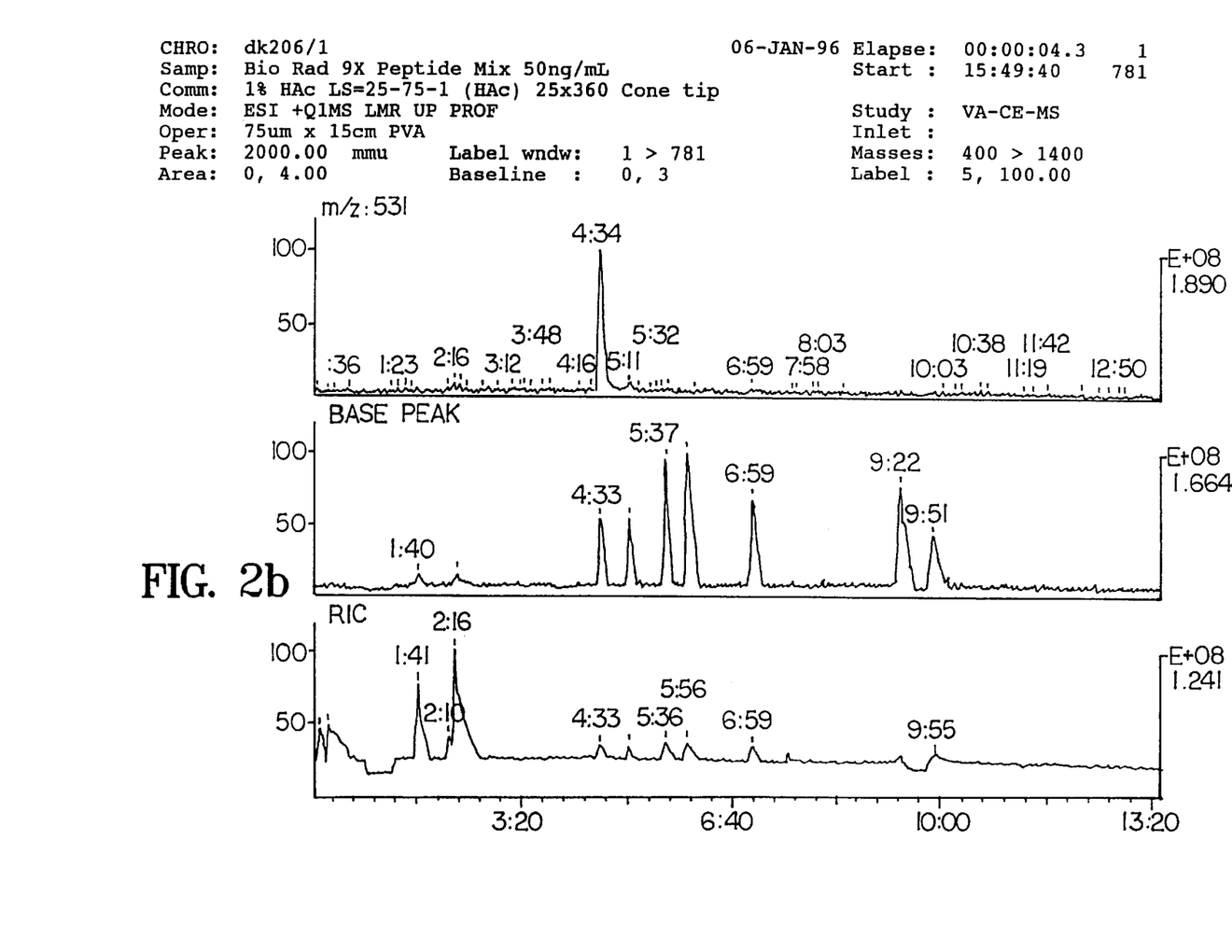

Capillary zone electrophoresis ESI-MS analysis of a peptide mixture, using the subatmospheric sample delivery chamber of the invention configured as an electrospray ionization interface, was carried out according to the method of the invention described herein. The applied sample consisted of Peptide Calibration Set No. 148-2012 from Bio-Rad Laboratories, Inc., a mixture of bradykinin, angiotensin II, α-MSH, TRH, LHRH, bombesin, leu-enkephalin, metenkephalin and oxytocin, at 50 ng/ml each. Capillary electrophoresis separation conditions were: [background electrolyte: 50 mM acetic acid; capillary: 75 $\mu$m id×15 cm, inside wall coated with a hydrophilic polymer to prevent adsorption and electroosmosis; constant current: 6 $\mu$A (8 kV); hydrodynamic injection, 5 s/5 cm]. Electrospray injection for mass spectrometry was accomplished using a fused silica electrospray needle (25 $\mu$m id×50 mm). Pressure in the subatmospheric chamber: 600 Torr. Electrospray voltage: ~1500 V generated by an electrophoresis power supply with a resistor of 250 MOhms. In FIG. 2a, the UV trace of the separated peptides, as monitored by fiber optic detector (28) is presented, and the corresponding total ion electropherogram and selected ion monitoring traces are shown in FIG. 2b.

Figure 3:
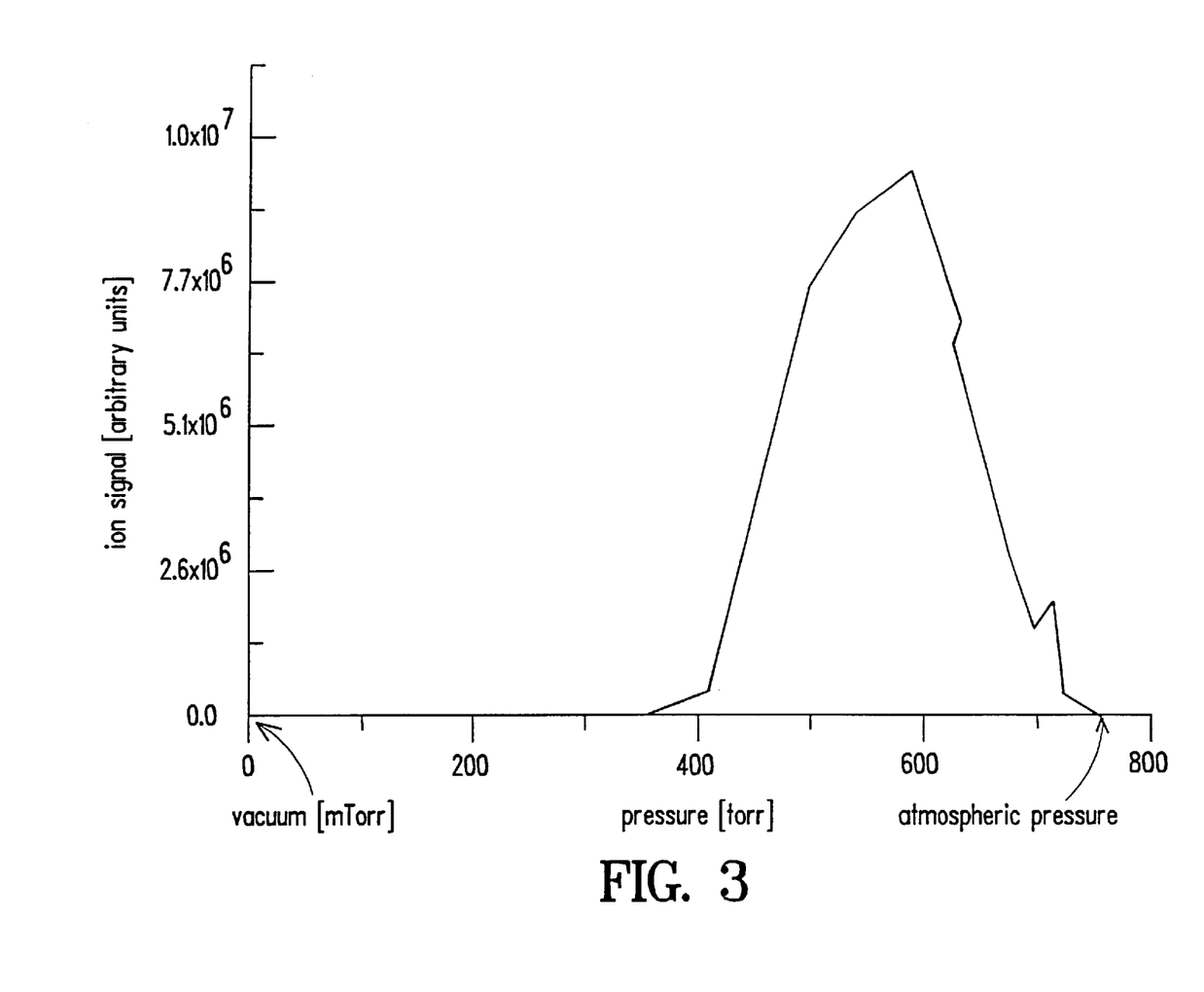

The optimum pressure for subatmospheric sample delivery chamber operation to produce the maximum ion signal, using the system shown in FIG. 1a, was determined by electrospray of a sample of bullfish angiotensin I at $10^{-5}$ M in 1.5% acetic acid and 50% methanol/$H_2O$ via an ESI needle having a tip i.d. of 24 $\mu$m and o.d. of 50 $\mu$m. The electrospray potential was 2.24 kV. Referring to FIG. 3, a plot of ion signal versus sample delivery chamber pressure shows a preferred operating range of 450–700 torr. The optimum pressure in the sample delivery chamber will depend on the gas intake capability of the mass spectrometer. This experiment was carried out using a mass spectrometer supplied by Finnigan Corporation (San Jose, Calif.), which, as supplied by the manufacturer, has a sampling orifice of ~0.4 mm in diameter. Generally, the wider the opening of the mass spectrometer sampling orifice, the higher the gas intake and the lower the optimum operating pressure can be in the subatmospheric chamber. If the sampling orifice diameter is tripled, optimun results could be provided with an order of magnitude lower pressure in the subatmospheric pressure (~50 Torr). It is contemplated that with even wider mass spectrometer sampling openings, a chamber pressure as low as 1 Torr could be optimum.

Figure 4:
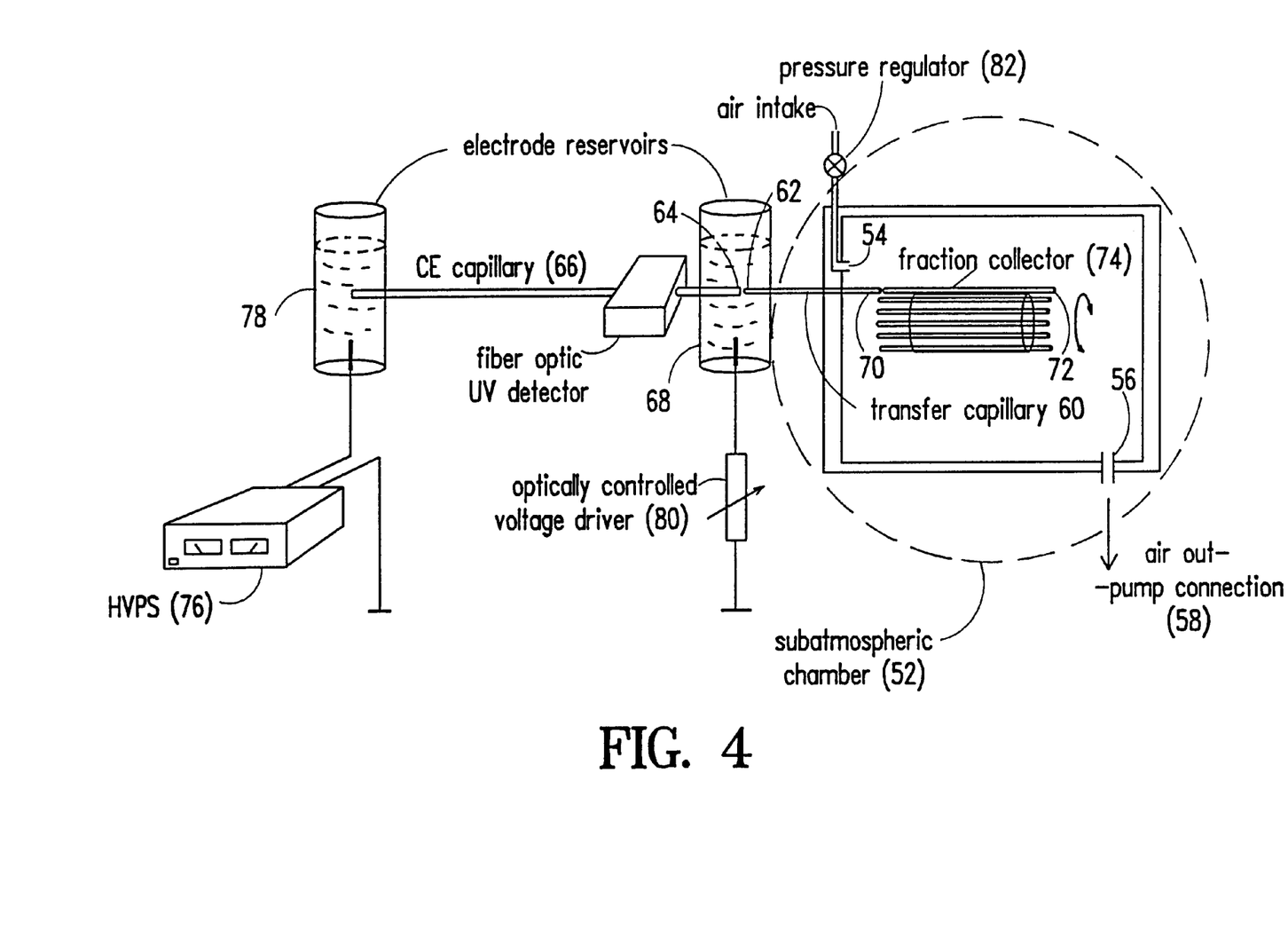
FIG. 4 is a section through a side schematic view of another embodiment of the invention.

A subatmospheric sample delivery chamber is also useful for direct delivery of a sample to a collection device. Referring to FIG. 4, a suitable system consists of a subatmospheric chamber (52), which has an inlet port (54), for introducing a gas into the chamber, and an exit port (56), coupled to a pump for gas removal (58). A sample delivery needle (60) extends from outside the chamber into the interior of the chamber. The inlet end (62) of sample delivery needle (60) is aligned with the exit end (64) of an electrophoresis capillary (66) in an electrode buffer reservoir (68). The exit end (70) of sample delivery needle (60) is aligned with a collection capillary (72) in fraction collector (84).

Capillary electrophoresis is conducted in electrophoresis capillary (66) under a current established via high voltage power supply (76), in contact with electrode buffer input reservoir (78), and an optically controlled voltage divider (80), in contact with electrode buffer output reservoir (68). The fluid from the electrode buffer output reservoir (68) flows into sample delivery needle (60) at inlet end (62) and towards exit end (70) due to the pressure difference between the reservoir (68) and subatmospheric chamber (52). This flow causes the ions exiting the outlet (64) of the CE capillary (66) also to enter the sample delivery needle. The fractions are then collected at the exit end (70) into collection vials (capillaries) (72) of the fraction collector (74). The pressure inside the subatmospheric chamber (52) is controlled by the pump (58) connected to the chamber outlet (56) and by the pressure regulator (82) connected to the chamber air inlet port (54). This arrangement assures that the transport of ions and fluid inside the CE capillary (66) is not affected by the changes of the flow into the sample delivery needle (60), which would occur if a positive pressure was applied at the electrode output buffer reservoir (68).

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An ionization interface for introducing a sample into an analytical device, said interface comprising:

a chamber configured to maintain a subatmospheric pressure between 1 and 750 Torr, said chamber having an inlet port for introducing a gas into said chamber and an exit port configured for attachment to an analytical device external to said chamber; and a sample delivery device extending from outside said chamber into the interior of said chamber, said delivery device having an inlet end and an exit end, wherein the inlet end of said delivery device is configured for receiving a sample for delivery into an analytical device, the exit end of said delivery device is configured for sample ionization and said exit end, furthermore, is aligned with the exit port of said chamber, and a gas input tube extending to said chamber from said inlet port at least partially surrounds said sample delivery device.

2. The ionization interface of claim 1 wherein said sample delivery device is a capillary tube.

3. The ionization interface of claim 1 wherein said sample delivery device is a microchip.

4. The ionization interface of claim 1 wherein the exit end of said sample delivery device is non-metallized.

5. The ionization interface of claim 1 wherein said exit end of said sample delivery device has an inside diameter that is less than the average inside diameter of a delivery passage through said delivery device.

6. The ionization interface of claim 1 wherein surface material of said sample delivery device surrounding an opening for fluid flow in said exit end of said sample delivery device is coated with a non-wetting, hydrophobic material.

7. The ionization interface of claim 1 further comprising a gas input valve for controlling introduction of gas into said chamber.

8. The ionization interface of claim 1 further comprising a pressure monitor for monitoring gas pressure inside said chamber.

9. The ionization interface of claim 1 wherein the inlet end of said delivery device is coupled to a device for conducting a microseparation technique.

10. The ionization interface of claim 9 wherein said device for conducting a microseparation technique is configured for capillary electrophoresis, capillary electrochromatography or microcolumn liquid chromatography.

11. The ionization interface of claim 1 wherein the exit end of said delivery device is configured for electrospray ionization of said sample.

12. The ionization interface of claim 1 wherein said analytical device is a mass spectrometer and said exit port of said chamber is capable of being coupled to a sampling orifice for a mass spectrometer.

13. A capillary electrophoresis/electrospray ionization interface system for introducing a sample into a mass spectrometer, said system comprising:

a separation capillary having an inlet end and an outlet end, said capillary having the capacity to separate a sample of molecules traversing said capillary from said inlet end to said outlet end in an electric field;

a first electrophoresis buffer reservoir positioned to provide electrophoresis buffer at said inlet end of said capillary, wherein an electrode connected to a high voltage power supply is in electrical contact with said first reservoir;

a second electrophoresis buffer reservoir positioned to provide electrophoresis buffer at said outlet end of said capillary, wherein an electrode connected to a variable resistor is in electrical contact with said second reservoir; and an electrospray ionization interface device, said device comprising a chamber configured to maintain a subatmospheric pressure between 1 and 750 Torr, said chamber having an inlet port for introducing a gas into said chamber and an exit port capable of being coupled to a sampling orifice for a mass spectrometer, and a sample delivery device extending from outside said chamber into the interior of said chamber, said delivery device having an inlet end and an exit end, wherein the inlet end of said delivery device is positioned to receive a sample exiting from the outlet end of said capillary and the exit end of said delivery device is configured for electrospray delivery of a sample traveling through said delivery device and said exit end, furthermore, is aligned with the exit port of said chamber.

14. A method for introducing a sample into a mass spectrometer, said method comprising the steps of:

providing a mass spectrometer, said mass spectrometer having a sampling orifice and a means for evacuating gas from said mass spectrometer;

providing an electrospray ionization interface device for introducing a sample into said mass spectrometer, said device comprising a chamber configured to maintain a subatmospheric pressure between 1 and 750 Torr, said chamber having an inlet port for introducing a gas into said chamber and an exit port coupled to the sampling orifice for said mass spectrometer, and a sample delivery device extending from outside said chamber into the interior of said chamber, said delivery device having an inlet end and an exit end, wherein the inlet end of said delivery device is configured for receiving a sample for delivery into a mass spectrometer and the exit end of said delivery device is configured for electrospray delivery of a sample traveling through said delivery device and said exit end, furthermore, is aligned with the exit port of said chamber;

removing gas from said mass spectrometer to obtain a gas pressure of less than 10 mTorr in said mass spectrometer;

regulating a flow of gas into said chamber via said inlet port so that gas pressure in said chamber is between 1 and 750 Torr;

introducing a sample into the inlet end of said sample delivery device;

causing ions in said sample to spray from the exit end of said sample delivery device in the direction of the sampling orifice of said mass spectrometer; and continuing to regulate said flow of gas into said chamber so that the flow pattern of said gas continuously directs said ions into the sampling orifice of said mass spectrometer.

15. A sample collection apparatus comprising a subatmospheric, variable pressure sample delivery chamber configured to maintain a subatmospheric pressure between 1 and 750 Torr, said chamber having an inlet port for introducing a gas into said chamber and an exit port coupled to a pump for removal of gas;

a collection device contained within said chamber; and a sample delivery device extending from outside said chamber into the interior of said chamber, said delivery device having an inlet end and an exit end, wherein the inlet end of said delivery device is configured for receiving a sample and the exit end of said delivery device is positioned to deliver a sample to said collection device, and wherein, further, said collection device is configured so that a sample delivered to said collection device is recoverable from said collection device outside said sample delivery chamber.

16. The sample collection apparatus of claim 15 wherein said sample delivery device is a capillary tube.

17. The sample collection apparatus of claim 15 wherein said sample delivery device is a microchip.

18. The sample collection apparatus of claim 15 wherein the exit end of said sample delivery device is non-metallized.

19. The sample collection apparatus of claim 15 wherein said exit end of said sample delivery device has an inside diameter that is less than the average inside diameter of a delivery passage through said delivery device.

20. The sample collection apparatus of claim 15 wherein surface material of said sample delivery device surrounding an opening for fluid flow in said exit end of said sample delivery device is coated with a non-wetting, hydrophobic material.

21. The sample collection apparatus of claim 15 further comprising a gas input tube extending into said chamber from said inlet port and partially contiguous with said sample delivery device.

22. The sample collection apparatus of claim 15 further comprising a gas input valve for controlling introduction of gas into said chamber.

23. The sample collection apparatus of claim 15 further comprising a pressure monitor for monitoring gas pressure inside said chamber.

24. The sample collection apparatus of claim 23 wherein said device for conducting a microseparation technique is configured for capillary electrophoresis, capillary electrochromatography or microcolumn liquid chromatography.

25. The sample collection apparatus of claim 15 coupled to a device for conducting a microseparation technique.

26. A method for delivering a sample to a collection device, said method comprising the steps of:
   providing a subatmospheric, variable pressure sample delivery chamber configured to maintain a subatmospheric pressure between 1 and 750 Torr, said chamber having an inlet port for introducing a gas into said chamber and an exit port coupled to a pump for removal of gas, said chamber further comprising a collection device inside said chamber and a sample delivery device extending from outside said chamber into the interior of said chamber, said delivery device having an inlet end and an exit end, wherein the inlet end of said delivery device is configured for receiving a sample and the exit end of said delivery device is aligned with said collection device, and wherein, further, said collection device is configured so that a sample delivered to said collection device is recoverable from said collection device outside said sample delivery chamber;
   removing gas from said chamber via said pump and regulating a flow of gas into said chamber via said inlet port so that gas pressure in said chamber is lower than gas pressure outside said chamber, gas pressure in said chamber being between 1 and 750 Torr; and
   introducing a sample into the inlet end of said sample delivery device, whereupon a pressure difference between the inlet end and the exit end of said sample delivery device causes said sample to travel between said inlet end and said exit end and to transfer from said exit end to said collection device.

27. A method for introducing a sample into an analytical device, said method comprising the steps of:
   providing an analytical device, said analytical device having a sampling orifice and a means for evacuating gas from said analytical device;
   providing an ionization interface for introducing a sample into said analytical device, said ionization interface comprising
      a chamber configured to maintain a subatmospheric pressure between 1 and 750 Torr, said chamber having an inlet port for introducing a gas into said chamber and an exit port coupled to the sampling orifice for said analytical device, and
      a sample delivery device extending from outside said chamber into the interior of said chamber, said delivery device having an inlet end and an exit end, wherein the inlet end of said delivery device is configured for receiving a sample for delivery into an analytical device and the exit end of said delivery device is configured for sample ionization and said exit end, furthermore, is aligned with the exit port of said chamber;
   removing gas from said analytical device to obtain a gas pressure of less than 10 mTorr in said analytical device;
   regulating a flow of gas into said chamber via said inlet port so that gas pressure in said chamber is between 1 and 750 Torr;
   introducing a sample into the inlet end of said sample delivery device;
   causing ions in said sample to spray from the exit end of said sample delivery device in the direction of the sampling orifice of said analytical device; and
   continuing to regulate said flow of gas into said chamber so that the flow pattern of said gas continuously directs said ions into the sampling orifice of said analytical device.

28. The method of claim 27 wherein the exit end of said delivery device is configured for electrospray ionization of said sample.

29. The method of claim 27 wherein said analytical device is a mass spectrometer and said exit port of said chamber is capable of being coupled to a sampling orifice for a mass spectrometer.

30. The method of claim 27 wherein said sample delivery device is a capillary tube.

31. The method of claim 27 wherein said sample-delivery device is a microchip.

32. The method of claim 27 wherein the exit end of said sample delivery device is non-metallized.

33. The method of claim 27 wherein said exit end of said sample delivery device has an inside diameter that is less than the average inside diameter of a delivery passage through said delivery device.

34. The method of claim 27 wherein surface material of said sample delivery device surrounding an opening for fluid flow in said exit end of said sample delivery device is coated with a non-wetting, hydrophobic material.

* * * * *